(12) United States Patent
Tam et al.

(10) Patent No.: US 9,855,115 B2
(45) Date of Patent: Jan. 2, 2018

(54) AUTOMATED ORTHODONTIC BRACKET POSITIONING SYSTEM AND METHOD

(71) Applicant: Weng Kie Tam, Kowloon (HK)

(72) Inventors: Weng Kong Tam, Kowloon (HK); Weng Kie Tam, Kowloon (HK)

(73) Assignee: Weng Kie Tam, Kowloon (HK)

( * ) Notice: Subject to any disclaimer, the term of this patent is extended or adjusted under 35 U.S.C. 154(b) by 9 days.

(21) Appl. No.: 14/789,667

(22) Filed: Jul. 1, 2015

(65) Prior Publication Data
US 2016/0000526 A1 Jan. 7, 2016

(30) Foreign Application Priority Data
Jul. 4, 2014 (CN) .......................... 2014 1 0316398

(51) Int. Cl.
| A61C 3/00 | (2006.01) |
|---|---|
| A61C 7/00 | (2006.01) |
| A61C 7/14 | (2006.01) |
| A61C 13/15 | (2006.01) |

(Continued)

(52) U.S. Cl.
CPC .............. *A61C 7/002* (2013.01); *A61C 7/146* (2013.01); *A61C 19/003* (2013.01); *A61C 9/0046* (2013.01); *A61C 19/05* (2013.01)

(58) Field of Classification Search
CPC .......... A61C 7/002; A61C 7/146; A61C 7/00; A61C 7/14; A61C 7/12; A61C 9/004; A61C 9/0006; A61C 19/004; A61C 19/003; A61C 19/00; A61C 19/05; A61C 19/04;

(Continued)

(56) References Cited

U.S. PATENT DOCUMENTS

| 4,579,380 A | * | 4/1986 | Zaremsky | .............. | B25J 13/082 |
|---|---|---|---|---|---|
| | | | | | 294/119.1 |
| 4,850,864 A | * | 7/1989 | Diamond | ............... | A61C 7/146 |
| | | | | | 33/513 |

(Continued)

FOREIGN PATENT DOCUMENTS

| CN | 102138829 A | 8/2011 | | |
|---|---|---|---|---|
| CN | 102481181 A | 5/2012 | | |
| DE | WO 0187179 A1 | * 11/2001 | .............. | A61C 7/146 |

OTHER PUBLICATIONS

Ganz, Scott D; Inside Dentistry. "The Next Evolution in CBCT: Combining Digital Technologies." vol. 9, Issue 2; Feb. 2013.*

(Continued)

*Primary Examiner* — Heidi M Eide
(74) *Attorney, Agent, or Firm* — Muncy, Geissler, Olds & Lowe, P.C.

(57) ABSTRACT

An automated orthodontic bracket positioning system including a computer system for constructing the digital 3D dental model, a bite record device for acquiring the patient's intra-oral coordinate record, and an automatic bracket positioning device for bonding orthodontic brackets on the patient's tooth surfaces or surfaces of dental cast. The computer system estimates a predicted position of each orthodontic bracket on patient's tooth surface or a surface of the gypsum dental cast by using the digital 3D dental model to control the automatic bracket positioning device to position the brackets on the patient's tooth surface or surfaces of the dental cast according to the predicted position.

8 Claims, 5 Drawing Sheets

(51) Int. Cl.
*A61C 9/00* (2006.01)
*A61C 19/05* (2006.01)

(58) Field of Classification Search
CPC . A61C 9/0046; A61C 2007/004; A61C 7/004; A61C 9/00
USPC .................................................... 433/24, 29
See application file for complete search history.

(56) References Cited

U.S. PATENT DOCUMENTS

| | | | |
|---|---|---|---|
| 8,366,442 B2* | 2/2013 | Schmitt | A61C 13/0004 378/170 |
| 2003/0204150 A1* | 10/2003 | Brunner | A61B 5/1114 600/590 |
| 2003/0215767 A1 | 11/2003 | Taub et al. | |
| 2006/0275736 A1* | 12/2006 | Wen | A61C 9/00 433/213 |
| 2008/0253506 A1* | 10/2008 | Zuendorf | A61B 6/14 378/18 |

OTHER PUBLICATIONS

Zhao Meng et al, "Model Measurement and Bracker Position System in Digital Three-Dimensional Dental Cast", Mar. 2008, Medical Information vol. 21. No. 3, pp. 1-4.

* cited by examiner

AUTOMATED ORTHODONTIC BRACKET POSITIONING SYSTEM AND METHOD

CROSS-REFERENCE TO RELATED APPLICATION

This application claims the benefit of China Patent Application No. 201410316398.X, filed on Jul. 4, 2014, the disclosure of which is incorporated herein in its entirety by reference, in the State Intellectual Property Office of the People's Republic of China.

BACKGROUND OF THE INVENTION

1. Field of the Invention

The present disclosure relates to an orthodontic field, more particularly to an automated system capable of accurately positioning orthodontic brackets on the patient's tooth surfaces or surfaces of a dental model.

2. Description of the Related Art

In orthodontic dentistry, it is found that the malocclusion of teeth affects development of normal function of the patient's mouth and reduces mastication efficiency of teeth, which results in problem of swallowing, indigestion and gastrointestinal disease. Severe tooth misalignment also affects growth of facial skeleton, temporo-mandibular joint and muscle, and causes facial asymmetry and undesirable language expression. Therefore, a negative effect may be produced on the patient's psychology. The maxillary and/or mandibular protrusion may cause that lips cannot be closed freely and undesirable mouth breathing. The oral plaque may be easily attached on misaligned dentition and hardly cleaned, so it easily causes dental decay, gingivitis and periodontitis.

Malocclusion is caused by the problem of the misaligned teeth or undesirable jaw relation. The orthodontic braces or brackets can be fastened on the tooth surface in order to fully achieve orthodontic effect. Brackets are bonded on tooth surfaces one by one, metal wires are engaged in the brackets, and the metal wires interact with the brackets to move the teeth into the desired positions.

Clinically, the bonding positions and orientations of the brackets relative to tooth's axes are highly depended on experiences and skills of dentists. The procedure of bonding the brackets on the tooth surfaces can be accomplished in two ways: direct and indirect bonding procedures. In the direct bonding procedure, the dentist bonds the brackets on the tooth surfaces one by one upon his/her experience and skill, but it consumes much chair time of the dentist. In addition, some regions inside the mouth (such as molar teeth or lingual surface of tooth) can hardly be visually accessed by the dentists that make the bracket bonding work difficult. The indirect procedure requires the patients' impression model taken by the dentist, and dental casts similar to patients' dentitions can be made based on the impression model. The dental technicians then bond the brackets on the dental casts in the laboratory. The positions of the bonded brackets will be recorded by using a custom impression tray. Clinically, the dentists can then transfer the position records and bond the brackets on patients' teeth.

Currently, the use of digital model is rapidly increasing in the orthodontic industry. The so-called digital model is a 3D digital dental cast which is constructed by using patient's intra-oral scan, computation, analysis and modeling, and the 3D digital dental cast can be transformed to a physical dental cast by a well-known technology (such as 3D printing). For dentist, the digital model is helpful for more correct dental diagnosis and orthodontics treatment planning, and also useful for predicting or simulating movements of the teeth and treatment result during the treatment.

The digital model can provide assistance however, each step of bonding the brackets on teeth by the direct bonding procedure or the indirect bonding procedure is still executed by the dentist. Actually, it is a difficult work. First, some regions (such as tooth at deep part of oral cavity or lingual surface) are hardly visible and touched. Next, bonding materials are time- and light-sensitive that they should be skillfully handled. The light-curing adhesive is adopted as the adhesive for bonding material and should be hardened not until the bracket is positioned correctly. If the material is hardened too early, it will have insufficient time for the brackets to be placed correctly. The brackets will be bonded at unexpected positions. Therefore, controlling the adhesive curing time is a challenge for dentist. Moreover, severe misaligned teeth may increase difficulty on positioning and fastening of the brackets, and cause the procedures hardly be achieved perfectly.

SUMMARY OF THE INVENTION

An objective of the present disclosure is to provide an automated orthodontic bracket positioning system capable of accurately positioning the orthodontic brackets on the patient's tooth surfaces via an automatic bracket positioning device provided with a digital 3D dental model.

The automated orthodontic bracket positioning system of the present disclosure includes a computer system for constructing the digital 3D dental model, a bite record device for acquiring the patient's intra-oral coordinate record, and an automatic bracket positioning device for bonding orthodontic brackets on the patient's tooth surfaces or surfaces of a dental cast. The computer system estimates a predicted position of each orthodontic bracket on patient's tooth surface or a surface of the dental cast by using the digital 3D dental model. The computer system, with the use of the bite record device, receives and utilizes the intra-oral coordinate record to calibrate the digital 3D dental model to match with the patient's practical condition, whereby the predicted positions can accurately correspond to the patient's tooth surfaces. The computer system controls the automatic bracket positioning device to position the brackets on the patient's tooth surfaces or surfaces of the dental cast according to the predicted positions.

The automatic bracket positioning device includes: a multi-joint robotic arm performing a multi-angle, multi-axle, and multi-curvature movement; a holder disposed at a distal toggle of the multi-joint robotic arm to hold or release a bracket; a light emitting module disposed on a distal toggle of the multi-joint robotic arm to provide a curing light to the brackets held by the holder for hardening the light-curing adhesive of the bracket.

The bite record device includes a bite recorder and a sensor for detecting the bite recorder. The bite recorder is coated with dental impression material on an upper surface and a lower surface thereof, and configured for steadily fastening the bite recorder on the dentition. The bite recorder has multiple calibrating markers located on preset locations. The sensor is disposed on the distal toggle or holder of the multi-joint robotic arm, and configured for detecting the calibrating markers to acquire the intra-oral coordinate record.

During the automated procedure of bonding the brackets on the patient's tooth surfaces, the bite recorder is placed in the patient's mouth to be lightly bitten by the patient's upper and lower dentitions. The sensor detects the calibrating markers. The calibrating markers are used as the patient's intra-oral reference points, the sensor detects the intra-oral reference points to generate multiple groups of digital point sets related to the space positions on tooth surfaces, and transmits the digital point sets to the computer system via a transmission line. The computer system executes a program computation to convert the digital point sets into an intra-oral coordinate record. The computer system then receives and utilizes the intra-oral coordinate record to calibrate the digital 3D dental model, to ensure that the computed coordinate of the digital 3D dental model match with the practical intra-oral coordinate. Therefore, the predicted positions of the brackets estimated by the computer system accurately correspond to the patient's tooth surface. In addition, when the automatic bracket positioning device transfers the bracket onto the patient's tooth surfaces, the computer system acquires the information of position relationship between the sensors and the calibrating markers, and then controls the multi-joint robotic arm according to the acquired information until the brackets are accurately transferred onto the tooth surfaces.

The automatic bracket positioning device, which is controlled by the computer system, can directly bonds the brackets on the patient's tooth surfaces (direct bonding procedure), or bonds the brackets on the surfaces of a physical dental cast (indirect bonding procedure). In the indirect bonding procedure, the bonding positions of the brackets can be recorded by the custom impression tray, and the dentist can transfer the brackets onto the patient's tooth via the impression tray clinically.

The automatic bracket positioning device further provides a light source to harden adhesive applied between the brackets and the tooth's surface. When the multi-joint robotic arm and the holder accurately move the brackets in touch with the patient's tooth surfaces or the surfaces of the dental cast, the light source is activated to harden the adhesive applied between the bracket and the surface, whereby the brackets can be bonded and fastened on the patient's tooth surfaces or the surfaces of the dental cast.

Other objective of the present disclosure is to provide a positioning method applied to an automated orthodontic bracket positioning system, comprising steps of: performing an extra-oral 3D scanning process to scan the teeth to obtain tooth models inside patient's mouth, or directly performing intra-oral 3D scanning process to scan the teeth, so as to obtain tooth shape information; using the bite record device in the mouth to record a tooth biting relation, and performing extra-oral 3D scanning process to scan the bite record device for obtaining tooth biting information and marker calibration information; transmitting the tooth shape information, the tooth biting information and the marker calibration information to the computer system, wherein the computer system constructs a digital 3D dental model according to the tooth shape information and the tooth biting information, and using the constructed digital 3D dental model to predict a position of a bracket on the tooth surface; placing the bite record device into the patient's mouth again to enable a tray of the bite recorder to be bitten by the patient's upper and lower dentitions, and using the sensor to detect marker calibration information, and transmitting the detected information to the computer system, wherein the computer system converts the detected information to an intra-oral coordinate record and then uses the intra-oral coordinate record to revise the digital 3D dental model for ensuring that a predicted position of the bracket accurately matches with the patient's tooth surface; controlling the control module to drive the holder to clamp the bracket and transfer the bracket to the tooth surface according to the predicted location by the computer system; using a curing light provided from a light emitting module of the computer to hard the bracket on the patient's tooth surface; and releasing the bracket from the holder by opening the multi-joint robotic arm driven by the control module controlled by the computer system.

The present disclosure has at least one of following advantages.

First, the automatic bracket positioning device which is connected with the computer system constructing the digital 3D dental model, can accurately position the orthodontic brackets onto the patient's tooth surfaces or the surfaces of the dental cast.

Secondly, the automated operation of bonding the brackets can shorten the required time and the procedure of bonding and fastening the brackets, so as to reduce burdens for dentist or the dental technician during the orthodontic process.

Thirdly, the regions hardly visible and contactable by the dentist can be accessed by using the holder and the multi-joint robotic arm, whereby the brackets can be easily bonded on the tooth surfaces which are hardly being accessed.

Fourthly, the adhesive applied between the brackets and the tooth's surface can be hardened at the most appropriate time points, the holder of the multi-joint robotic arm can hold the brackets firmly before light-curing and release immediately after the adhesive is completely hardened.

Fifthly, the automatic bracket positioning device replaces the process of the dentist manually bonding and fastening the brackets on the tooth surfaces, so that the manual burden of the dentist and the difficulty of traditional orthodontics process can be reduced.

Sixthly, the computer system directs, controls, commands and manages the holder and the multi-joint robotic arm of the automatic bracket positioning device, so that the brackets can be automatically taken out from the bracket tray one by one and accurately bonded on the patient's tooth surfaces or the surfaces of the dental cast one by one.

Seventhly, the orthodontics procedure is almost executed by the computer system, the holder, the multi-joint robotic arm automatically. Therefore, the dentist and the dental technician serve as monitors to monitor the operations of whole automated system.

BRIEF DESCRIPTION OF THE DRAWINGS

The detailed structure, operating principle and effects of the present disclosure will now be described in more details hereinafter with reference to the accompanying drawings that show various embodiments of the present disclosure as follows.

DETAILED DESCRIPTION OF THE PREFERRED EMBODIMENTS

Reference will now be made in detail to the exemplary embodiments of the present disclosure, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this disclosure will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts.

It will be understood that, although the terms 'first', 'second', 'third', etc., may be used herein to describe various elements, these elements should not be limited by these terms. The terms are used only for the purpose of distinguishing one component from another component. Thus, a first element discussed below could be termed a second element without departing from the teachings of embodiments. As used herein, the term "or" includes any and all combinations of one or more of the associated listed items.

Figure 1:
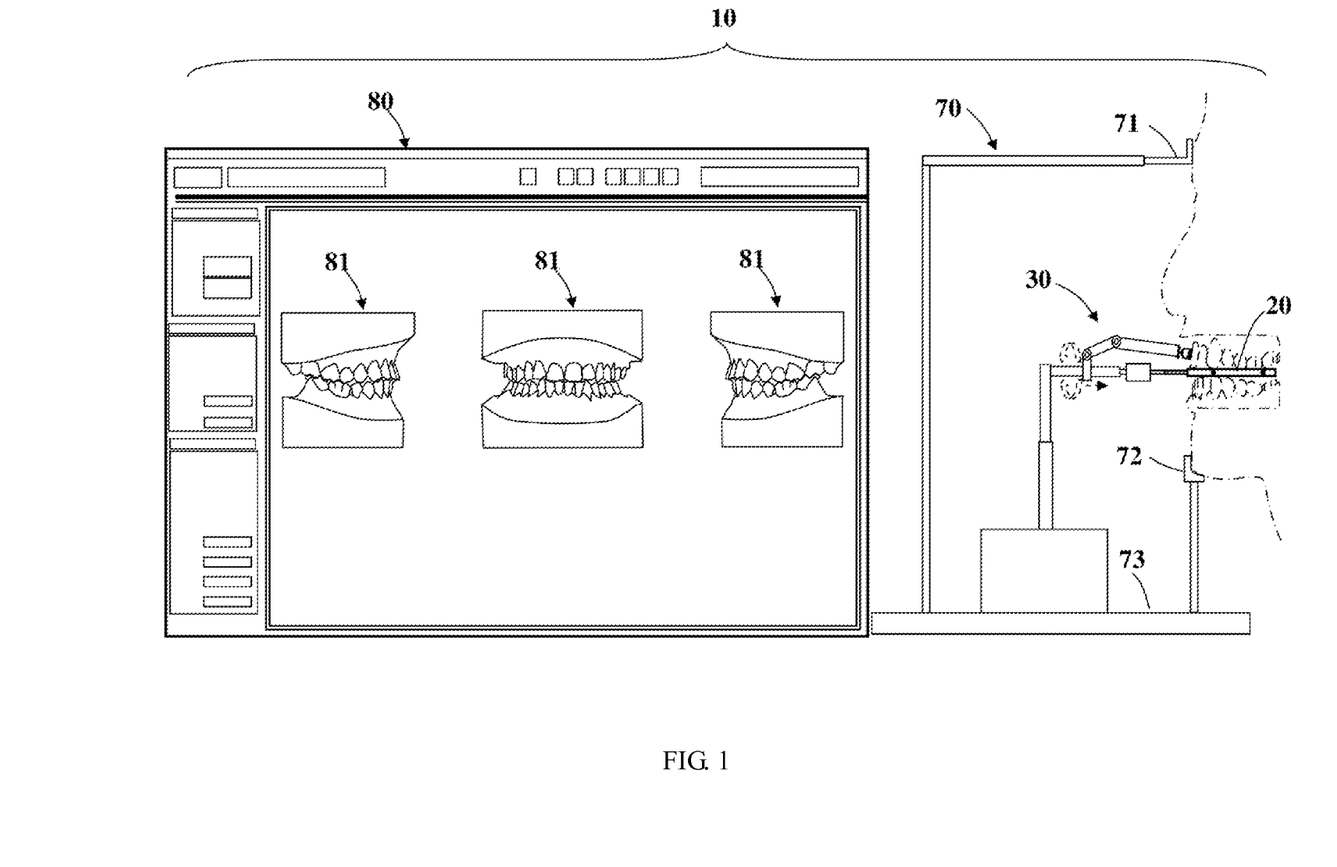
FIG. 1 is a schematic view of automated orthodontic bracket positioning system of the present disclosure.

As shown in FIG. 1, the automated orthodontic bracket positioning system 10 of the present disclosure includes a bite record device 2, an automatic bracket positioning device 30 and a computer system 80. The bite recorder 20 is coupled with the automatic bracket positioning device 30 and the computer system 80.

The computer system 80 is configured for constructing a digital 3D dental model, and the technology of building the digital 3D dental model 81 is a well-known technology, such as contact-type measurement technology, intra-oral scan technology, or chromatography, incorporating with software program computation and analysis, so as to acquire the orientation and coordinate data of the teeth of patient's upper and lower dentitions, and information of position relationship between the mandible and the maxilla. The computer system 80 estimates a predicted position of each orthodontic bracket on patient's tooth surface or a surface of the dental cast by using the digital 3D dental model. The computer system 80 controls the automatic bracket positioning device 30 to position the brackets 32 on the patient's tooth surfaces or the surfaces of the dental cast according to the predicted positions (please refer to FIG. 4).

Figure 2:
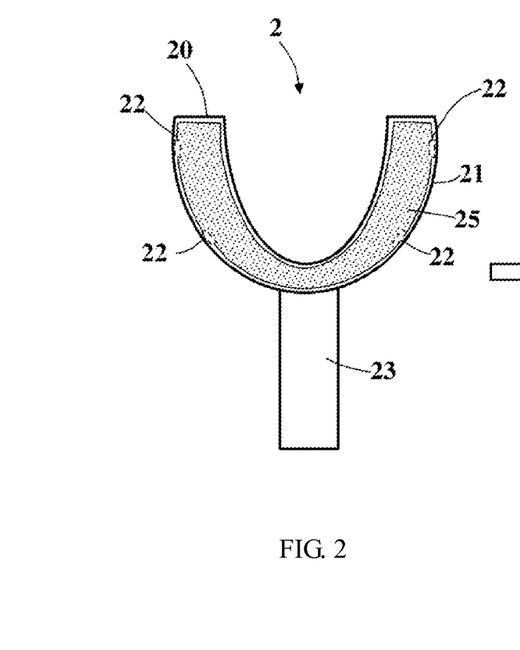
FIG. 2 is a structural schematic view of a bite recorder of the present disclosure.
Figure 3:
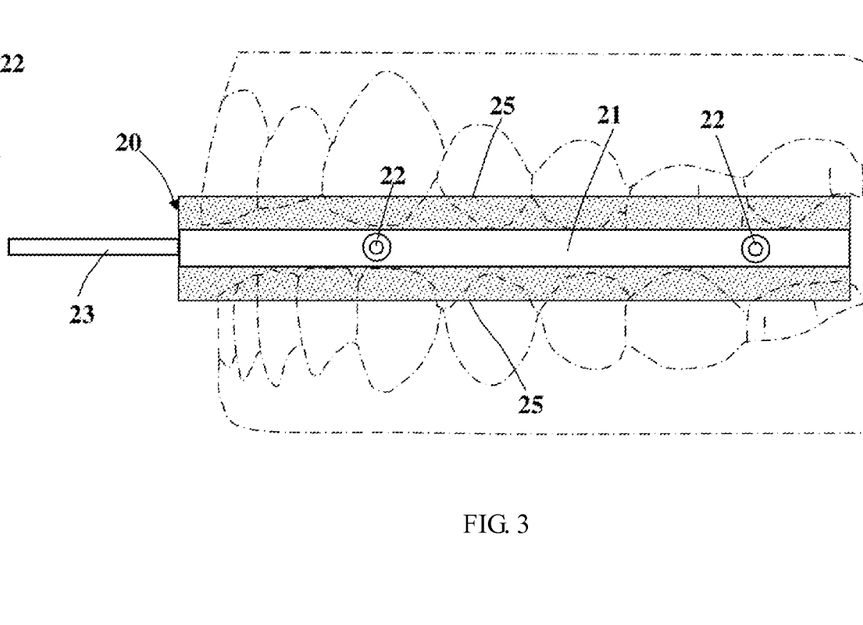
FIG. 3 is a schematic view of the bite recorder in the patient's mouth, in accordance with the present disclosure.

The bite record device 2 includes a bite recorder 20 and a sensor 24 for detecting the bite recorder 20. As shown in the embodiment of FIG. 2 and FIG. 3, the bite recorder 20 is a sturdy tray 21 in flat arc shape. The tray 21 is pre-coated with dental impression material 25 on both surfaces thereof. The tray 21 is placed into the patient's mouth to be lightly bitten by the patient's upper and lower dentitions, and the bite condition of the tooth can be recorded via the dental impression material 25 and the bite recorder 20 is steadily fastened on the dentition and hardly shifted in the patient's mouth, so as to ensure the subsequent detection to be precisely executed. The tray 21 is provided with calibrating markers 22 respectively disposed at multiple preset positions. A connector 23 is assembled at a front end of the tray 21 and extended outwardly. The connector 23 is not inserted into the patient's mouth. The connector 23 is connected with the automatic bracket positioning device 30 and the computer system 80. The sensor 24 is disposed at a distal toggle 62 or a holder 31 of a multi-joint robotic arm 61 of the automatic bracket positioning device 30, and configured for detecting the calibrating markers 22 which are used as intra-oral reference point in the patient's mouth. The sensor 24 detects the intra-oral reference points to generate multiple groups of digital point sets related to the space positions on tooth surfaces, and transmits the digital point sets to the computer system 80 via a transmission line (not shown in FIGs). The computer system executes a program computation to convert the digital point sets into an intra-oral coordinate record. The computer system then receives and utilizes the intra-oral coordinate record to calibrate the digital 3D dental model, to ensure the practical intra-oral coordinate to match with the computation coordinate of the digital 3D dental model. Therefore, the predicted positions of the brackets estimated by the computer system can accurately match with the patient's tooth surfaces. In addition, when the automatic bracket positioning device 30 transfers the bracket 32 onto the patient's tooth surface, the computer system acquires the information of position relationship between the sensors 24 and the calibrating markers 22 according to information collected by the sensors 24, and then controls the multi-joint robotic arm 61 according to the acquired information until the bracket 32 is accurately transferred onto the tooth surface according to the predicted position.

Figure 4:
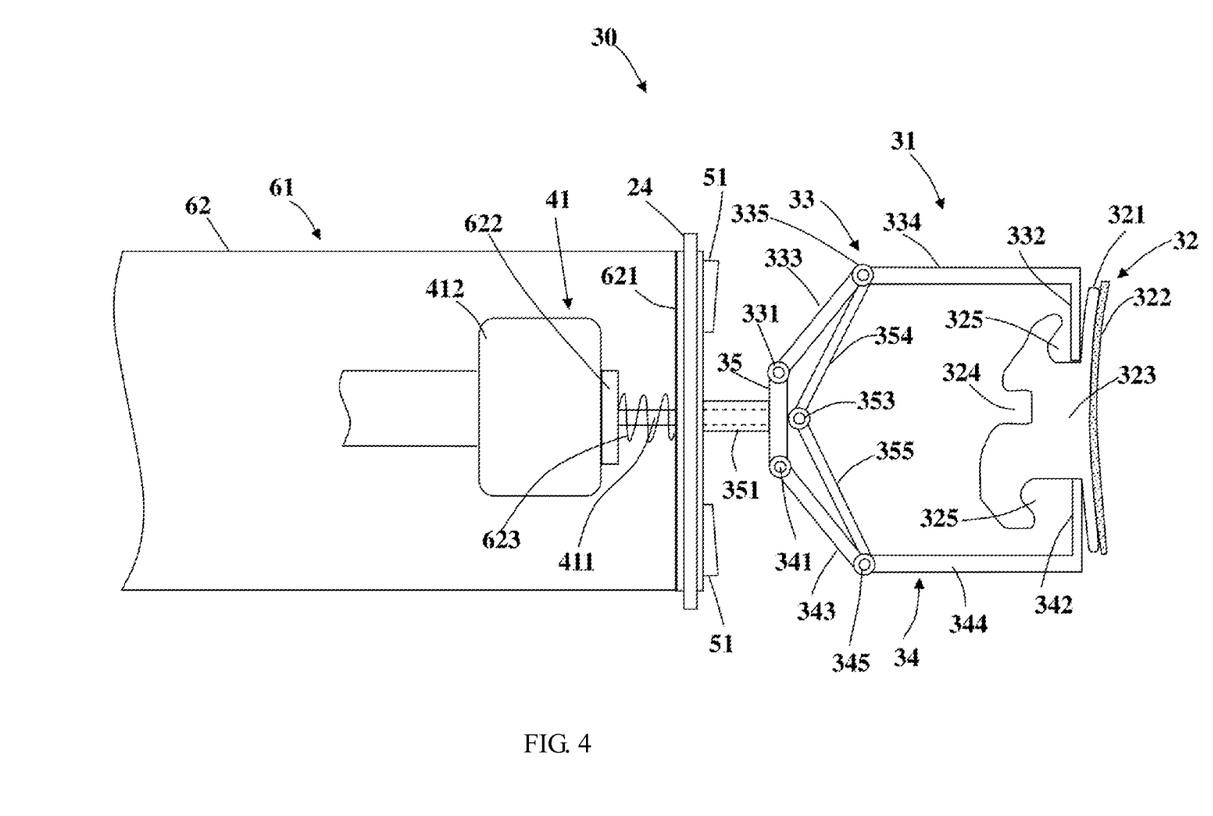
FIG. 4 is a first structural schematic view of the automatic bracket positioning device of the present disclosure.
Figure 5:
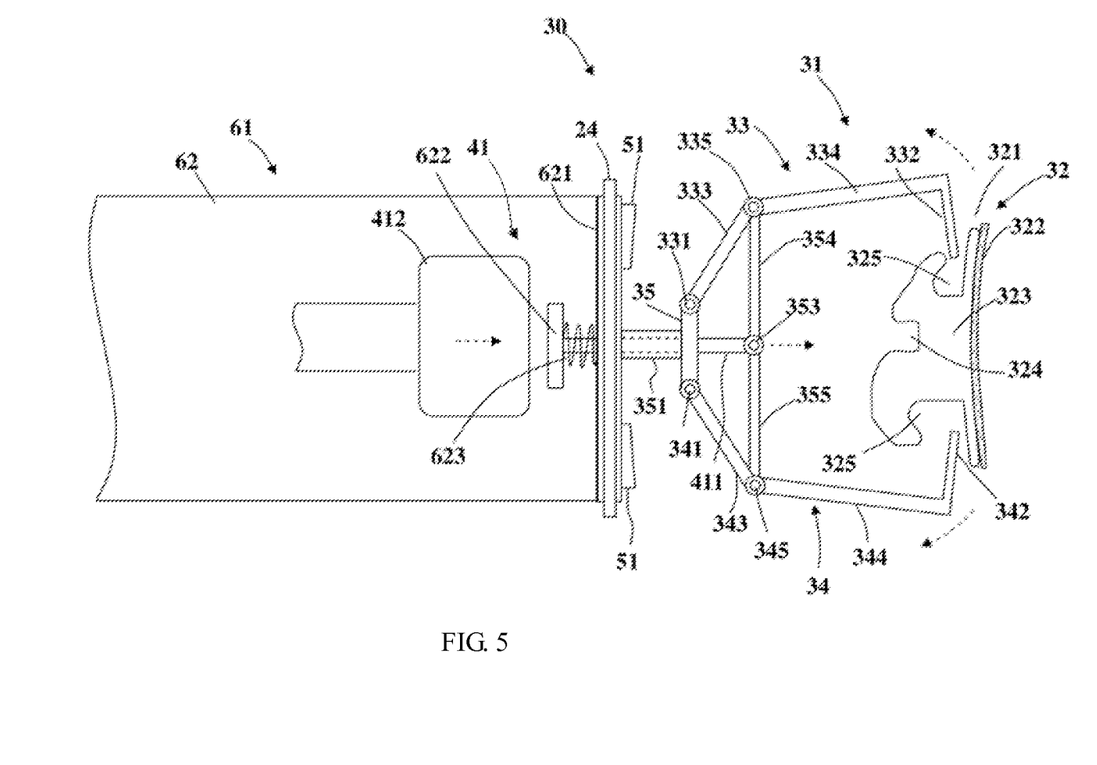
FIG. 5 is second structural schematic view of the automatic bracket positioning device of the present disclosure.

As shown in FIG. 4 and FIG. 5. The automatic bracket positioning device 30 includes a holder 31, a control module 41, a light emitting module 51 and a multi-joint robotic arm 61.

The holder 31 is configured for holding or releasing a bracket 32. The bracket 32 is an existing physical structure and includes a base 321. A side of the base 321 is coated a layer of light-curing adhesive 322, and the base 321 is provided with a body 323 at other side thereof. The body 323 is provided with a wire slot 324 at a center part thereof for receiving a metal wire, and provided with recessed parts 325 at two opposite sides thereof respectively for receiving the holder 31. The holder 31 is provided with a first arm 33 and a second arm 34, first ends of the first arm 33 and the second arm 34 are linked to a positioning plate 35 via a rotating pivot 331 and 341, and second ends of the first arm 33 and the second arm 34 are provided with fastening members 332 and 342 which can fasten or release a recessed part 325 of the holder 31. The first arm 33 and the second arm 34 are provided with first rods 333 and 343 and second rods 334 and 344 respectively. The first rods 333 and 343, and the second rods 334 and 344 are linked and fastened with each other via an axis. The positioning plate 35 is linked and fastened with the distal toggle 62 of the multi-joint robotic arm 61 via a structural component 351.

The control module 41 includes an actuating rod 411 and an actuator 412 which is used for controlling the actuating rod 411 to reciprocate. The actuating rod 411 is inserted axially through the structural component 351, a first end of the actuating rod 411 is passed through the end plate 621 of the distal toggle 62 and inserted into the distal toggle 62, and an inner end of the actuating rod 411 is linked with a contact member 622. A reset spring 623 is mounted on the actuating rod 411 between the contact member 622 and the end plate 621. A second end of the actuating rod 411 is passed through the positioning plate 35, and linked with first ends of a first support rod 354 and a second support rod 355. The first support rod 354 and the second support rod 355 are linked with an axis 353. A second end of the first support rod 354 is linked with an axis 335 of the first arm 33, and a second end of the second support rod 355 is linked with an axis 345 of the second arm 34.

According to the above-mentioned content, when the actuating rod 411 reciprocates along the axis of the structural component 351, the linear motion of the actuating rod 411 is converted to the linkage motions of the first arm 33 and the second arm 34 via the first support rod 354 and the second support rod 355, so that the fastening member 332 and 342 can be fastened with or released from a recessed part 325 of the bracket 32. Accordingly, the holder 31 can hold or release the bracket 32.

The actuator 412 is disposed within the distal toggle 62 of the multi-joint robotic arm 61 and the actuator 412 can be a mechanical assembly or a magnetic assembly. As shown in FIGs, the actuator 412 is a magnetic assembly and coupled with the computer system 80 via a coil and a conductive wire. The computer system 80 directs, controls and commands the actuator 412 to exert a pushing force on the contact member 622 or relieve the pushing force for the contact member 622. When the pushing force is exerted on the contact member 622, the actuating rod 411 is moved toward the holder 31 to compress the reset spring 623 to enable the holder 31 to release the bracket 32. When the pushing force is relieved, the contact member 622 is restored by the reset spring 623 to drive the actuating rod 411 to move in reverse, so that the holder 31 can be closed to nip the bracket 32.

The light emitting module 51 is disposed on the end plate 621 of the distal toggle 62 of the multi joint robotic arm 61, and coupled with the computer system 80. The computer system 80 directs, controls and commands the light emitting module 51 to turn on or off. The light emitting module 51 provides a curing light toward the light-curing adhesive 322. The curing light is used to harden the light-curing adhesive 322 of the brackets 32.

The multi joint robotic arm 61 is directed, controlled and commanded by the computer system 80 to execute a multi-angle, multi-axle and multi-curvature movement, in cooperation with the linking operation of the holder 31 and the control module 41, to pick up the brackets 32 from the bracket tray (not shown in FIGs) and place the brackets 32 on the patient's tooth surfaces according to the predicted positions estimated by the computer system 80. The brackets 32 are prepared in the bracket tray, one by one, following the tooth sequence in four quarters, upper-left, upper-right, lower-left and lower-right regions. This is a well-known arrangement.

The multi-joint robotic arm 61 is provided with a pressure sensor (not shown in FIGs). When the bracket 32 is placed onto the patient's tooth surface, a counterforce is transmitted to the multi-joint robotic arm 61. When the pressure sensor detects the pressure reaching a predetermined value, it indicates that the bracket 32 is stably touched with the patient's tooth surface already. In the meantime, the computer system 80 activates the light emitting module 51 to irradiate curing light to harden the light-curing adhesive 322, whereby the bracket 32 can be bolded on the patient's tooth surface. Later, the computer system 80 commands the control module 41 to operate to enable the holder 31 to open, so that the holder 31 can be separated from the bracket 32 located on the patient's tooth surface.

Figure 6:
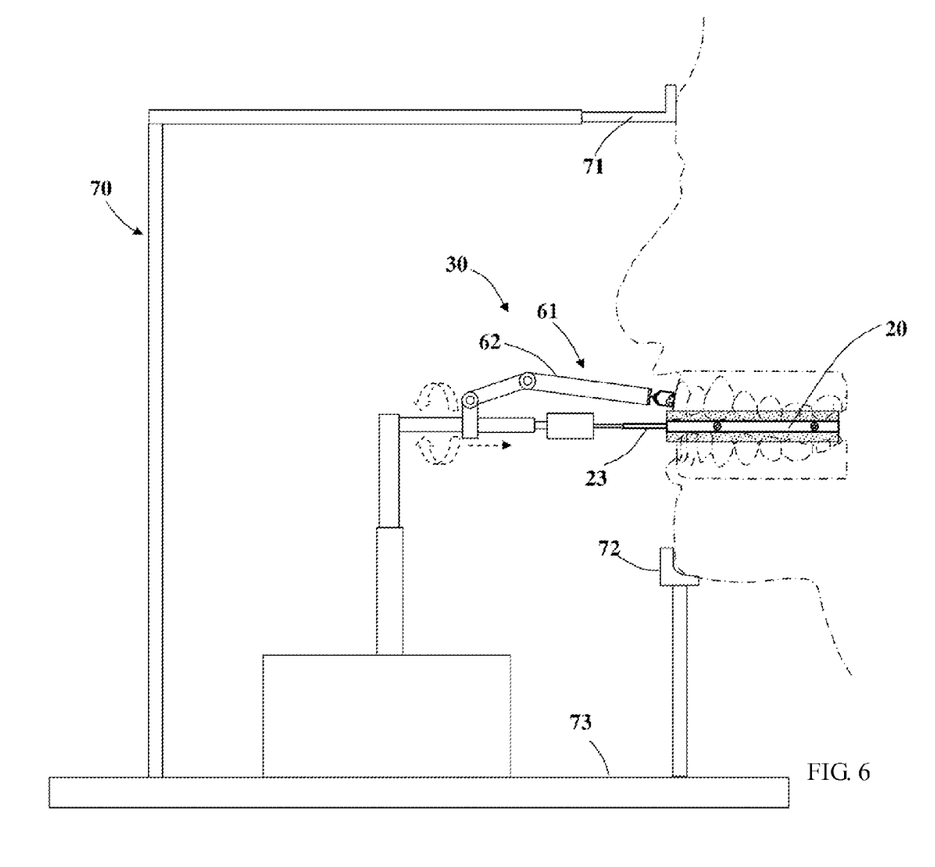
FIG. 6 is a schematic view showing position relationship among the automatic bracket positioning device, head support and the patient's head, in accordance with the present disclosure.

Please refer to FIG. 6. In order to accurately bond the brackets 32 on the patient's tooth surfaces, it is necessary to hold the patient's head. A head support 70 is used in the present disclosure, and the head support 70 includes a forehead guide 71 and a chin guide 72. The forehead guide 71 is located above the automatic bracket positioning device 30, the chin guide 72 is located below the automatic bracket positioning device 30, and the forehead guide 71 and the chin guide 72 are fastened in a base 73. During the process of bonding the bracket 32 on the patient's tooth surface, the patient's chin is held by the chin guide 72 and the patient's forehead is contacted with the forehead guide 71, so as to keep the patient's head being at an upright status. During the process of placing the bracket 32, the patient must keep biting the bite recorder 20, and the patient's lip is appropriately opened by a dental lip retractor to enable the teeth to be exposed possibly. In front of the patient, the automatic bracket positioning device 30 places the brackets 32 on the patient's tooth surfaces one by one, and then the dentist engages metal wires on the brackets 32. The metal wires interact with the brackets to move the teeth into the desired positions for a preset period of time.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. An automated orthodontic bracket positioning system, comprising:
   a computer system, configured for constructing a digital 3D dental model, and the computer system predicting positions of orthodontic brackets on patient's tooth surface based upon the 3D dental model;
   an automatic bracket positioning device, coupled with the computer system and controlled by the computer system; the automatic bracket positioning device comprising a multi-joint robotic arm capable of performing a multi-angle, multi-axle, and multi-curvature movement; a holder disposed at a remote toggle of the multi joint robotic arm to hold or release a bracket;
   a bite record device, coupled with the computer system, and comprising a bite recorder and a sensor; wherein the bite recorder comprising a tray for being bitten by the patient's upper and lower dentitions, and at least two calibrating markers disposed on the tray and positionable inside the mouth; wherein the sensor is mounted on the automatic bracket positioning device and in communication with the bite record device via calibrating markers located on the bite recorder; the computer system executing a program computation to convert a detected message of the bite record device to an intra-oral coordinate record, and then using the intra-oral coordinate record to calibrate the digital 3D dental model, to ensure that the predicted position of the bracket accurately match with the patient's tooth surface, the automatic bracket positioning device connected with the bite recorder and transferring bracket onto the patient's tooth surface according to the predicted position; and
   a light emitting module, disposed at the remote toggle of the multi joint robotic arm, the light emitting module configured for providing a curing light to harden light-curing adhesive on the bracket held by the holder and positioned on the patient's tooth surface.

2. The automated orthodontic bracket positioning system as defined in claim 1, wherein the holder is provided with a first arm and a second arm, first ends of the first arm and the second arm are linked to the remote toggle via a rotating pivot, and second ends of the first arm and the second arm are provided with fastening members which can fasten or release a recessed part of the bracket; a control module, disposed at the remote toggle and connected to the first arm and the second arm, and the control module configured for controlling an open-close operation of the first arm and the second arm to enable the fastening members to fasten or release the recessed part of the bracket.

3. The automated orthodontic bracket positioning system as defined in claim 2, wherein the control module comprises an actuating rod linked with the remote toggle and an actuator disposed at the remote toggle and linked with the actuating rod to reciprocate; an end of the actuating rod is linked with first ends of a first support rod and a second support rod via a rotating pivot, and second ends of the first support rod and the second support rod are respectively linked with the first arm and the second arm.

4. The automated orthodontic bracket positioning system as defined in claim 3, wherein another end of the actuating rod is linked to a contact member, the actuator is linked with the actuating rod via the contact member and configured for controlling the actuating rod to reciprocate, and a reset spring is mounted on the actuating rod between the contact member and an end of the remote toggle.

5. The automated orthodontic bracket positioning system as defined in any one of claim 1 to claim 4, wherein the automated orthodontic bracket positioning system further comprises a head support to hold and position the patient's head, and the head support comprises a forehead guide located above the automatic bracket positioning device and a chin guide located below the automatic bracket positioning device, and the forehead guide and the chin guide are mounted on a base, the forehead guide is configured for contacting with the patient's forehead, and the chin guide is configured for holding the patient's chin.

6. The automated orthodontic bracket positioning system as defined in any one of claim 1 to claim 4, further comprising: a pressure sensor disposed on the multi-joint robotic arm and configured for detecting a counterforce occurred while the bracket is placed on the tooth surface.

7. The automated orthodontic bracket positioning system as defined in claim 1, wherein the tray of the bite recorder is pre-coated a preset thickness of dental impression material on an upper surface and a lower surface thereof.

8. A positioning method applied to an automated orthodontic bracket positioning system, comprising steps of:
  obtaining tooth models inside a patient's mouth by performing an extra-oral 3D scanning process to scan the teeth, or directly performing intra-oral 3D scanning process to scan the teeth, so as to obtain tooth shape information;
  using the bite record device having at least two calibrating markers disposed on a tray and positionable inside the mouth to record a tooth biting relation, and performing extra-oral 3D scanning process to scan the bite record device for obtaining tooth biting information and marker calibration information;
  transmitting the tooth shape information, the tooth biting information and the marker calibration information to a computer system, wherein the computer system constructs a digital 3D dental model according to the tooth shape information and the tooth biting information, and predicts a position of a bracket on the tooth surface by using the constructed digital 3D dental model;
  placing the bite record device into the patient's mouth again to enable the tray of the bite record device to be bitten by the patient's upper and lower dentitions, and using a sensor to detect marker calibration information, and transmitting the detected information to the computer system, wherein the computer system converts the detected information to an intra-oral coordinate record and then uses the intra-oral coordinate record to revise the digital 3D dental model for ensuring that a predicted position of the bracket accurately matches with the patient's tooth surface;
  using the computer system to control a control module to drive a holder to clamp the bracket and transfer the bracket to the tooth surface according to the predicted location;
  hardening the bracket on the patient's tooth surface with a light-curing adhesive by a curing light provided from a light emitting module of the computer system; and
  releasing the bracket from the holder by opening a multi joint robotic arm driven by the control module controlled by the computer system.

* * * * *